(12) United States Patent
Nishio et al.

(10) Patent No.: US 10,420,876 B2
(45) Date of Patent: Sep. 24, 2019

(54) CENTRIFUGAL SEPARATION METHOD

(71) Applicant: FUJIFILM Corporation, Tokyo (JP)

(72) Inventors: Tomonori Nishio, Ashigarakami-gun (JP); Kazuteru Nishijima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 547 days.

(21) Appl. No.: 15/269,237

(22) Filed: Sep. 19, 2016

(65) Prior Publication Data

US 2017/0000941 A1 Jan. 5, 2017

Related U.S. Application Data

(63) Continuation of application No. 14/850,543, filed on Sep. 10, 2015, now abandoned, which is a
(Continued)

(30) Foreign Application Priority Data

Mar. 29, 2013 (JP) .................................. 2013-070995
Mar. 10, 2014 (JP) .................................. 2014-046087

(51) Int. Cl.
*A61M 1/36* (2006.01)
*B04B 1/02* (2006.01)
(Continued)

(52) U.S. Cl.
CPC .............. *A61M 1/3693* (2013.01); *A61J 1/05* (2013.01); *B01D 17/0217* (2013.01); *B04B 1/02* (2013.01);
(Continued)

(58) Field of Classification Search
CPC ...... B01L 3/50; B01L 3/5021; B01L 3/50215; B01L 2300/0864; B01L 2300/0858;
(Continued)

(56) References Cited

U.S. PATENT DOCUMENTS

| | | |
|---|---|---|
| 2,822,126 A | 2/1958 | Cohn |
| 7,947,186 B2 | 5/2011 | Soares et al. |
| (Continued) | | |

FOREIGN PATENT DOCUMENTS

| | | |
|---|---|---|
| JP | 2001-239185 A | 9/2001 |
| WO | 2010/036387 A2 | 4/2010 |

OTHER PUBLICATIONS

International Search Report issued in PCT/JP2014/058274 dated Jul. 15, 2014.
(Continued)

*Primary Examiner* — Walter D. Griffin
*Assistant Examiner* — Shuyi S. Liu
(74) *Attorney, Agent, or Firm* — Birch, Stewart, Kolasch & Birch, LLP

(57) ABSTRACT

A storage portion forming a storage space 10, includes an inclined inner wall portion 20 that is connected to a base portion so that the diameter of the inclined inner wall portion gradually decreases; a concave portion 22 is formed at a part of the inclined inner wall portion; and the concave portion 22 includes a concave portion side surface 22b that is connected to a concave portion bottom surface 22a. The concave portion 22 is formed at a position, where the concave portion crosses an interface S between the specimen centrifuged during rotation and air, in a radial direction with respect to the central axis; and the maximum width of the concave portion 22 in a circumferential direction around the central axis is included in a range of 2 mm to a length of 20% of the whole circumference.

19 Claims, 11 Drawing Sheets

Related U.S. Application Data continuation of application No. PCT/JP2014/058274, filed on Mar. 25, 2014.

(51) Int. Cl.
*B04B 7/08* (2006.01)
*B04B 9/14* (2006.01)
*B04B 5/04* (2006.01)
*B01D 17/02* (2006.01)
*A61J 1/05* (2006.01)
*B04B 1/08* (2006.01)
*B04B 11/04* (2006.01)

(52) U.S. Cl.
CPC .............. *B04B 1/08* (2013.01); *B04B 5/0407* (2013.01); *B04B 7/08* (2013.01); *B04B 9/14* (2013.01); *B04B 11/04* (2013.01)

(58) Field of Classification Search
CPC ...... G01N 33/491; B04B 5/0407; B04B 1/02; B04B 1/04; B04B 1/08; B04B 9/14; B04B 7/08; B04B 7/12; B04B 7/14; B04B 11/04; B01D 17/0217; A61M 1/3693; A61J 1/05
USPC ............ 494/37, 43, 56, 59, 60, 67; 422/547, 422/548, 527, 72; 210/360.1, 380.1, 515
See application file for complete search history.

(56) References Cited

U.S. PATENT DOCUMENTS

| | | |
|---|---|---|
| 8,177,072 B2 | 5/2012 | Chapman et al. |
| 2009/0259145 A1 | 10/2009 | Bartfeld et al. |
| 2011/0086752 A1 | 4/2011 | Brierton |

OTHER PUBLICATIONS

Written Opinion of the International Searching Authority issued in PCT/JP2014/058274 dated Jul. 15, 2014 (PCT/ISA/237).
Non-Final Office Action dated Mar. 25, 2016, issued in U.S. Appl. No. 14/850,543.

CENTRIFUGAL SEPARATION METHOD

CROSS-REFERENCE TO RELATED APPLICATIONS

This application is a Continuation of U.S. patent application Ser. No. 14/850,543 filed Sep. 10, 2015, which is a Continuation of PCT International Application No. PCT/JP2014/058274 filed on Mar. 25, 2014, which claims priority under 35 U.S.C § 119(a) to Patent Application No. 2013-070995 filed in Japan on Mar. 29, 2013 and Patent Application No. 2014-046087 filed in Japan on Mar. 10, 2014, all of which are hereby expressly incorporated by reference into the present application.

BACKGROUND OF THE INVENTION

1. Field of the Invention

The present invention relates to a centrifugal separation container, a centrifugal separation device that centrifugally separates components of a specimen present in a container by rotating the container about a central axis of the container as a rotation axis, and a centrifugal separation method using the centrifugal separation container and the centrifugal separation device.

2. Description of the Related Art

A centrifugal separation method of centrifugally separating components of a specimen, such as blood, present in a container by rotating the container has been known in the related art. In this centrifugal separation method, a centrifugal separation container, which includes an inner wall inclined so as to rise toward the outer periphery from the center and includes a storage portion forming a storage space storing a specimen in the container, is used and the container is rotated after a specimen is injected into the storage space. Further, components having a low specific gravity in the respective components of the specimen are separated first by a centrifugal force, which is caused by the rotation of the container, so that the components sequentially form a layer structure toward an outer peripheral side from an inner peripheral side. After that, when the rotation of the container stops, a low specific gravity component present on the inner peripheral side is generally released from the layer structure body and is stored on the bottom of the container.

However, when the centrifugal separation container in the related art is used, a low specific gravity component is not significantly released from the layer structure body even when the rotation of the container stops. For this reason, there is a problem in that considerable time is required until a low specific gravity component is stored on the bottom of the container. Particularly, when blood is centrifugally separated, a solvent may be applied to the inner wall of the container for the prevention of hemolysis. However, since the solvent causes the low specific gravity component (blood plasma) to be not easily released, the above-mentioned problem is significant. Further, since the amount of a specimen to be treated in the centrifugal separation container at a time as described above is in the range of 600 µL to 800 µL, the amount of a specimen, which can be recovered, is reduced when the centrifugal separated components stick to the inside of the storage portion. For this reason, a problem that the necessary amount of a specimen cannot be recovered may also occur.

Accordingly, various methods have been proposed in order to improve the recovery efficiency of a low specific gravity component. For example, JP2001-239185A discloses a method of facilitating the release of a low specific gravity component from the layer structure body by inducing the capillary phenomenon of a low specific gravity component using a centrifugal separation container that includes capillary phenomenon inducing structures formed on an inner wall surface of a storage portion thereof. Further, U.S. Pat. No. 7,947,186B discloses a method of facilitating the flow of a low specific gravity component and facilitating the release of a low specific gravity component from the layer structure body by using a centrifugal separation container that includes a hydrophilic region and a hydrophobic region formed on an inner wall surface of a storage portion.

SUMMARY OF THE INVENTION

However, since a capillary phenomenon is used in the method disclosed in JP2001-239185A, there is a limit to the induction rate of the low specific gravity component. For this reason, it cannot be said that recovery efficiency is sufficient in terms of time required to recover components. Meanwhile, in the method disclosed in U.S. Pat. No. 7,947,186B, a hydrophilic region having a predetermined shape is formed using a gel film on the storage portion. However, it is not easy to separately form the hydrophilic region and the hydrophobic region in appropriate shapes. Accordingly, processes for manufacturing the container are complicated in this method. For this reason, there is still a problem in that manufacturing costs of the container are increased.

The invention has been made in consideration of the above-mentioned problems, and an object of the invention is to provide a centrifugal separation container and a centrifugal separation method that can more efficiently recover centrifugally separated components of a specimen.

In order to solve the above-mentioned problems, according to an aspect of the invention, there is provided a centrifugal separation container that is used in a method of centrifugally separating a first specific gravity component and a second specific gravity component, of which a specific gravity of the second gravity component is higher than a specific gravity of the first specific gravity component, contained in a specimen injected into a storage space by rotating a container about a central axis of the container as a rotation axis. The centrifugal separation container includes a storage portion that forms the storage space. The storage portion includes an inclined inner wall portion of which a diameter gradually decreases from an upper end toward a lower end thereof and the lower end is connected to a base portion; a concave portion is formed at a part of the inclined inner wall portion; the concave portion includes a concave portion side surface that is connected to a concave portion bottom surface with a width of the concave portion gradually decreases toward the concave portion bottom surface from the inclined inner wall portion; the concave portion is formed at a position, where the concave portion crosses an interface between the specimen centrifuged during rotation and air, in a radial direction with respect to the central axis; and the maximum width of the concave portion in a circumferential direction around the central axis is included in a range of 2 mm to a length of 20% of the whole circumference passing through the concave portion having a center on the central axis.

In the centrifugal separation container according to the aspect of the invention, it is preferable that a connecting portion between the inclined inner wall portion and the concave portion side surface has a curvature. Further, it is preferable that a connecting portion between the concave portion side surface and the concave portion bottom surface has a curvature.

Furthermore, in the centrifugal separation container according to the aspect of the invention, it is preferable that a mean depth of the concave portion is 0.5 mm or more and it is preferable that the maximum depth of the concave portion is in the range of 0.5 mm to 2 mm. It is preferable that the maximum width of the concave portion is 10 mm or less.

Moreover, in the centrifugal separation container according to the aspect of the invention, it is preferable that the concave portion has the shape of a fan.

Further, the centrifugal separation container according to the aspect of the invention can employ a structure in which one concave portion is formed. In this case, it is preferable that the centrifugal separation container further includes a balancing portion that offsets a deviation of the center of gravity from the central axis caused by the formation of the concave portion to balance the container. It is preferable that the balancing portion is provided on the inclined inner wall portion at a position symmetrical to the position of the concave portion with respect to the central axis.

Alternatively, the centrifugal separation container according to the aspect of the invention can employ a structure in which two to four concave portions are formed. In this case, it is preferable that the concave portions are evenly disposed in the circumferential direction.

Further, in the centrifugal separation container according to the aspect of the invention, it is preferable that the maximum length of the concave portion is in the range of 5 mm to 15 mm.

Furthermore, in the centrifugal separation container according to the aspect of the invention, it is preferable that the concave portion is formed from the uppermost portion of the inclined inner wall portion.

Moreover, in the centrifugal separation container according to the aspect of the invention, it is preferable that the storage portion includes a trap portion that is connected to an upper end of the inclined inner wall portion and forms a trap space housing the second specific gravity component when the specimen is centrifugally separated and a layer structure body is formed on an outer peripheral side of the storage space.

Further, in the centrifugal separation container according to the aspect of the invention, it is preferable that a thixotropic separating agent having a specific gravity between the specific gravity of the first specific gravity component and the specific gravity of the second specific gravity component is provided in the storage space.

A centrifugal separation device according to another aspect of the invention includes the above-mentioned centrifugal separation container, and a container holder that rotates about a central axis of the container as a rotation axis while holding the container.

In addition, a centrifugal separation method according to still another aspect of the invention includes injecting a specimen into the above-mentioned centrifugal separation container, and centrifugally separating a first specific gravity component and a second specific gravity component contained in the specimen by rotating the container about a central axis of the container as a rotation axis.

In the centrifugal separation container of the invention, a concave portion is formed at a part of the inclined inner wall portion, includes a concave portion side surface that is connected to the concave portion bottom surface with a width of the concave portion gradually decreases toward the concave portion bottom surface from the inclined inner wall portion, has a sufficiently large width, and is formed at a position, where the concave portion crosses an interface between the specimen centrifuged during rotation and air, in a radial direction with respect to the central axis. According to the container of the invention, a portion of the first specific gravity component, which is present above the concave portion, is more easily released from the layer structure body than portions of the first specific gravity component that are present in other regions. Accordingly, a portion of the first specific gravity component, which is present above the concave portion, is released first from the layer structure body, and portions of the first specific gravity component, which are present in other regions, are released from the layer structure body so as to be pulled to the portion of the first specific gravity component, which is present above the concave portion, due to the release of the portion of the first specific gravity component present above the concave portion. The concave portion can be easily formed simultaneously with the molding of the container. As a result, centrifugally separated components of the specimen can be more efficiently recovered.

Further, since centrifugal separation is performed using the centrifugal separation container of the invention in the centrifugal separation device and the centrifugal separation method of the invention, centrifugally separated components of the specimen can be more efficiently recovered.

DESCRIPTION OF THE PREFERRED EMBODIMENTS

Figure 1:
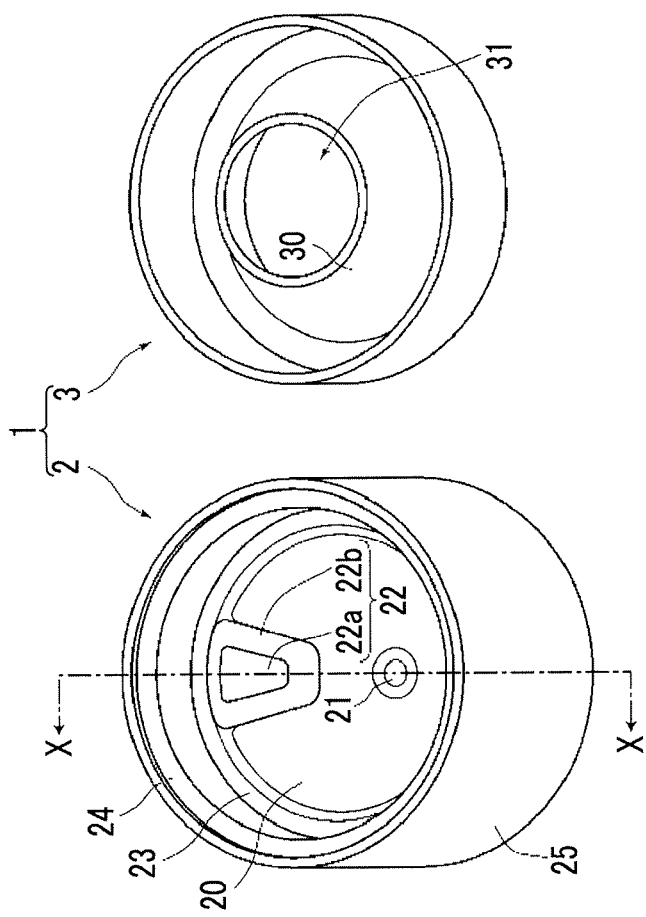
FIGS. 1A to 1C are schematic views showing the structure of a centrifugal separation container according to an embodiment.

An embodiment of the invention will be described below with reference to the drawings, but the invention is not limited to the embodiment. Meanwhile, for easy visual recognition, the scale and the like of each of components shown in the drawings are made to be appropriately different from the actual scale and the like.

FIGS. 1A to 1C are schematic views showing the structure of a centrifugal separation container I according to the embodiment. Particularly, FIG. 1A is a perspective view of a body member 2 of the container 1, FIG. 1B is a perspective view of a lid member 3 of the container 1, and FIG. 1C is an enlarged view of a concave portion 22 formed at an inclined inner wall portion 20 of the body member 2. Further, FIG. 2 is a schematic sectional view of the body member 2 of the container 1 taken along line X-X of FIG. 1, and FIG. 3 is a schematic sectional view showing the internal structure of the container 1 taken along line X-X.

Figure 2:
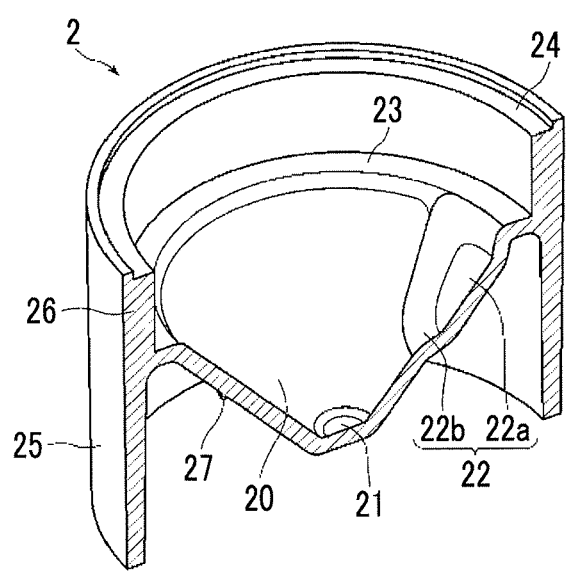
FIG. 2 is a schematic sectional view of a body member of the container taken along line X-X of FIG. 1.
Figure 3:
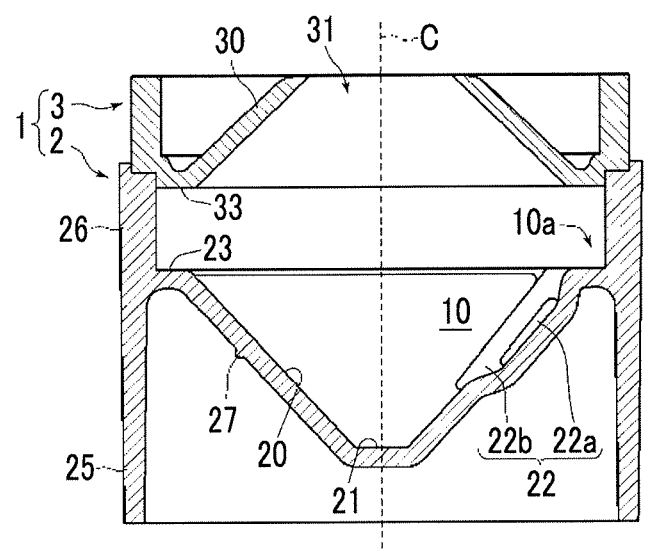
FIG. 3 is a schematic sectional view showing the internal structure of the container taken along line X-X of FIG. 1.

The container 1 according to this embodiment includes the body member 2 and the lid member 3 of the container as shown in FIGS. 1 to 3. The body member 2 includes an inclined inner wall portion 20, a base portion 21, a trap bottom surface portion 23, a trap side surface portion 26, a fitting portion 24 that is fitted to the lid member 3, and an outer support wall portion 25 that supports these portions. The lid member 3 includes an opening portion 30 that forms an opening 31 through which a specimen is injected, and a trap upper surface portion 33 that forms a trap space 10a together with the trap bottom surface portion 23 and the trap side surface portion 26 when being fitted to the body member 2.

The container 1 has an internal structure substantially axisymmetric with respect to an axis (a central axis C of the container), which passes through the center of the base portion 21 and is perpendicular to the base portion 21, (in other words, a structure like a sort of rotating body having a center on the central axis C), and has a substantially columnar appearance as a whole. When centrifugal separation is performed, the lid member 3 is, for example, fixed to the fitting portion 24 while being fitted to the fitting portion 24 of the body member 2 and the container 1 is rotated about the central axis C as a rotation axis.

When the body member 2 and the lid member 3 are fitted to each other, a storage space 10 into which a specimen is injected is formed as shown in FIG. 3. Specifically, the storage space 10 is a space that is surrounded by the inclined inner wall portion 20, the base portion 21, the trap bottom surface portion 23, the trap side surface portion 26, the trap upper surface portion 33, and the opening portion 30. Particularly, a space 10a, which is formed by the trap bottom surface portion 23, the trap side surface portion 26, and the trap upper surface portion 33, of the storage space serves as a trap space that traps a component of the specimen having high specific gravity when the container is rotated to centrifuge the specimen. That is, the inclined inner wall portion 20, the base portion 21, the trap bottom surface portion 23, the trap side surface portion 26, the trap upper surface portion 33, and the opening portion 30 correspond to a storage portion of the invention; and the trap bottom surface portion 23, the trap side surface portion 26, and the trap upper surface portion 33 correspond to a trap portion of the invention.

The inclined inner wall portion 20 includes an inclined surface which is formed in a substantially conical shape and of which a diameter is reduced toward a lower end of the inclined surface connected to the base portion 21 from an upper end thereof connected to the trap bottom surface portion 23. A lower portion of the storage space 10 is formed by the inclined surface. Further, a part of the inclined inner wall portion 20 forms the concave portion 22. The concave portion 22 includes a concave portion side surface 22b that allows the width of the concave portion 22 to gradually decreases toward a concave portion bottom surface 22a from the inclined inner wall portion 20 and is connected to the concave portion bottom surface 22a. It is preferable that a connecting portion between the inclined inner wall portion 20 and the concave portion side surface 22b has a curvature to prevent the hemolysis of the specimen and a connecting portion between the concave portion bottom surface 22a and the concave portion side surface 22b has a curvature. Further details of the concave portion 22 will be described below. Further, the inclined inner wall portion 20 includes a protrusion 27 at a position symmetrical to the concave portion 22 with respect to the central axis C.

The protrusion 27 is to adjust the position of the center of gravity of the container 1 that is changed due to the formation of the concave portion 22 of the inclined inner wall portion 20, and corresponds to a balancing portion of the invention. Only one concave portion 22 has been formed at an inclined inner wall portion 20 in this embodiment. However, since only one concave portion 22 is formed, the position of the center of gravity of the container 1 according to this embodiment may deviate from the central axis of the container in design. Since the rotation of the container 1 becomes unstable in this case, it is not preferable that only one concave portion 22 is formed. Accordingly, since the protrusion 27 is provided in this embodiment to offset a difference in the moment of inertia that is caused since a part (concave portion) of the inclined inner wall portion 20 becomes distant from the central axis C, the mass of a portion symmetrical to the position of the concave portion 22 with respect to the central axis C is increased. Further, the balancing portion only has to balance the container and is not limited to the protrusion-shaped structure. For example, a structure in which a high-density material is embedded in the inclined inner wall portion 20 at a position symmetrical to the position of the concave portion 22 with respect to the central axis C may be employed as the balancing portion. Furthermore, the balancing portion may not be provided on the inclined inner wall portion 20 and may be provided on the outer support wall portion 25. Meanwhile, the balancing portion is not essential in the invention, and does not need to be provided, for example, when the above-mentioned deviation of the center of gravity does not occur originally or when the deviation of the center of gravity is negligibly small in regard to centrifugal separation. Examples of a case in which the deviation of the center of gravity does not occur may include a case in which a plurality of concave portions are disposed so as to be balanced, and a case in which the thickness of a portion of the inclined inner wall portion 20 corresponding to a concave portion is adjusted to be small even if one concave portion is formed.

The base portion 21 connected to the lower end of the inclined inner wall portion 20 includes a substantially horizontal flat surface that is connected to the lower end of the inclined surface of the inclined inner wall portion 20 so as to have a curvature. The flat surface forms the bottom surface of the storage space 10 in this embodiment, but the base portion 21 of the invention does not need to be flat and may be a rising curved surface. Since the container 1 is rotated about the central axis C, a specimen present near the central axis C tends to be hardly centrifugally separated. However, when the base portion 21 is formed of a rising curved surface, the centrifugal separation performance of the container can be further improved. The reason for this is as follows: when the base portion 21 is formed of a rising curved surface, a force in a direction away from the central axis C (which is a gravity component along the curved surface) is applied to a specimen present near the base portion 21 at the time of the injection of a specimen. As a result, since the specimen present near the base portion 21 is likely to be separated from the central axis C without staying near the central axis C during the rotation of the container 1, a centrifugal force is more efficiently applied to the specimen.

The trap bottom surface portion 23 connected to the upper end of the inclined inner wall portion 20 includes a substantially horizontal flat surface that is connected to the upper end of the inclined surface of the inclined inner wall portion 20 so as to have a curvature. The flat surface forms the bottom surface of the trap space 10a. The trap side surface portion 26 includes a perpendicular surface that is connected to the flat surface of the trap bottom surface portion 23 so as to be perpendicular to the flat surface of the trap bottom surface portion 23. The perpendicular surface forms the side surface of the trap space 10a.

The trap space 10a has an annular shape having a center on the central axis C, and the volume of the trap space 10a is designed according to the amount of a specimen to be injected. Further, a separating agent (or separation gel) is disposed, for example, in the trap space 10a in advance. The separating agent is appropriately selected from materials, which have an intermediate specific gravity between the specific gravities of the components, according to a low specific gravity component (first specific gravity component) and a high specific gravity component (second specific gravity component) that are contained in the specimen and are to be separated. Specifically, when blood plasma (low specific gravity component) and blood cells (high specific gravity component) contained in blood are to be separated, a material having an intermediate specific gravity between the specific gravity of the blood plasma and the specific gravity of the blood cell may be selected as the separating agent.

The outer support wall portion 25 extends downward from the trap side surface portion 26 while surrounding the entire inclined inner wall portion 20, and a lower end of the outer support wall portion 25 extends downward further than the base portion 21. Accordingly, the body member 2 is stably supported.

The opening portion 30 of the lid member 3 has, for example, a truncated conical shape and includes an inclined surface of which a diameter is reduced toward the opening 31. An upper portion of the storage space 10 is formed by the inclined surface. In this embodiment, the container 1 is rotated while the opening 31 is open. However, the opening may be adapted to be capable of being opened and closed as necessary. The trap upper surface portion 33 connected to the lower end of the opening portion 30 includes a substantially horizontal flat surface that is connected to the lower end of the inclined surface of the opening portion 30 so as to have a curvature. The flat surface forms the upper surface of the trap space 10a.

Figure 4:
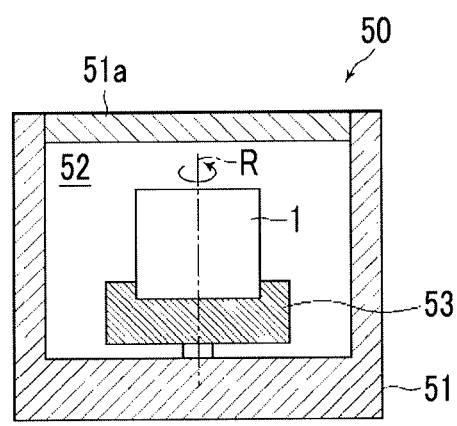
FIG. 4 is a schematic sectional view showing the structure of a centrifugal separation device.

Further, centrifugal separation is performed by, for example, a centrifugal separation device 50 shown in FIG. 4. The centrifugal separation device 50 includes an opening/closing lid 51a, a housing 51 that forms a housing space 52 housing the container 1, and a rotating table 53 (container holder) which is provided in the housing space 52 and on which the container 1 is mounted. The container 1 is brought into the housing space 52 while the opening/closing lid 51a is open, and is mounted on the rotating table 53. The rotating table 53 is supported to be rotatable by a rotating mechanism (not shown) (for example, a motor or the like), and rotates the container 1 so that the central axis C of the container 1 mounted on the rotating table 53 corresponds to a rotation axis R.

Figure 5:
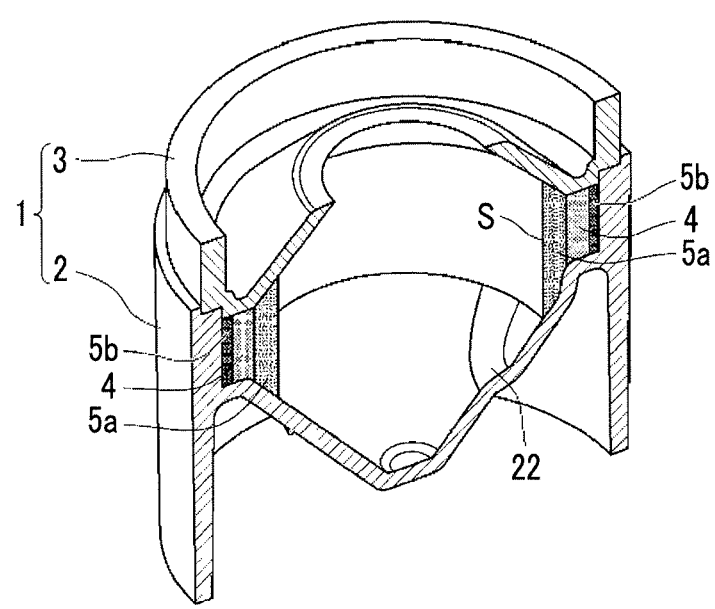
FIG. 5 is a schematic sectional view showing an internal state of the container during centrifugal separation.

The concave portion 22 of the inclined inner wall portion 20 will be described. FIG. 5 is a schematic sectional view showing an internal state of the container during centrifugal separation. FIG. 5 shows a state in which a layer structure body as a product of centrifugal separation is formed in an outer peripheral region of the storage space 10 as a result of the centrifugal separation of a specimen including a low specific gravity component (first specific gravity component) 5a and a high specific gravity component (second specific gravity component) 5b. The layer structure body has a structure in which the low specific gravity component 5a, the separating agent 4, and the high specific gravity component 5b are stacked from the inner peripheral side in this order. As shown in FIG. 5, the concave portion 22 is formed at a position, where the concave portion 22 crosses an interface S between the specimen centrifuged during rotation (particularly, the low specific gravity component 5a after centrifugal separation) and air, in the radial direction with respect to the central axis C. Accordingly, a portion of the low specific gravity component 5a present on the concave portion 22 is more easily released from the layer structure body than portions of the low specific gravity component 5a present in other regions. Since it is possible to easily form the concave portion 22 simply by adjusting the shape of a mold when the body member 2 is manufactured by injection molding or the like, an increase of the manufacturing cost of the container is not caused. Further, the concave portion 22 includes the concave portion side surface 22b in this embodiment, but the concave portion side surface 22b may be formed integrally with the concave portion bottom surface 22a. Furthermore, each of the concave portion side surface 22b and the concave portion side surface 22a may be formed of a curved surface.

It is preferable that the shape of the concave portion 22 is a fan shape having a center on the central axis C (including a truncated fan shape of which a portion including a central portion is cut out) so that an obstacle occurring when the specimen is centrifuged or when the low specific gravity component moves downward along the inclined surface of the inclined inner wall portion 20 is reduced. A fan shape (circular sector) of the invention means a shape of which at least a part includes a side parallel to a radial direction in a top view, and each corner of the fan shape may be rounded. Further, it is preferable that a side, which mainly extends in the circumferential direction around the central axis C, has an arc shape in the circumferential direction. Meanwhile, the concave portion 22 includes the flat bottom surface 22a along the inclined surface of the inclined inner wall portion 20 in this embodiment, but the bottom of the concave portion 22 is not limited to a flat surface.

The maximum width W1 (FIG. 1C) of the concave portion 22 in the circumferential direction around the central axis C is set to be sufficiently larger than a width, which causes a capillary phenomenon between the specimen and the concave portion, to facilitate the release of the low specific gravity component 5a from the layer structure body. For example, it is preferable that the maximum width W1 of the concave portion 22 is 2 mm or more and it is more preferable that the maximum width W1 of the concave portion 22 is 3 mm or more. Further, if a releasing force is locally generated when the low specific gravity component is released from the layer structure body, the release is facilitated. Furthermore, in order to easily balance the container, it is preferable that the maximum width W1 is equal to or smaller than 20% of the length of the entire circumference of the inclined inner wall portion in the circumferential direction around the central axis C at a position corresponding to the maximum width of the concave portion, that is, a length corresponding to 20% of an angular range of the concave portion. Moreover, considering the size of a general centrifugal separation container, it is preferable that the maximum width W1 is 10 mm or less and it is particularly preferable that the maximum width W1 is 8 mm or less.

Further, the maximum length W2 (FIG. 1C) of the concave portion 22 in the radial direction with respect to the central axis C in a top view is not particularly limited as long as the concave portion 22 crosses the interface S. Meanwhile, the maximum length W2 means a length along the inclined surface of the inclined inner wall portion 20. Generally, the maximum value and the minimum value of the amount of a specimen available to be used are determined as specifications of each centrifugal separation container. Accordingly, if a condition in which the concave portion 22 crosses the interface S is satisfied in regard to the amount of a specimen within the range of the specifications, it is generally sufficient. Therefore, an upper end of the concave portion 22 may be set to be on the side (outer peripheral side) above the position of the interface when the amount of a specimen is the lower limit of the range of the specifications, and a lower end of the concave portion 22 may be set to be on the side (inner peripheral side) below the position of the interface when the amount of a specimen is the upper limit of the range of the specifications. However, to prevent the hemolysis of the specimen caused by the concave portion 22 and to easily balance the container when the specimen is centrifuged, it is preferable that the maximum length W2 is in the range of 5 mm to 15 mm and is in the range of 6 mm to 12 mm and it is more preferable that the maximum length W2 is in the range of 7 mm to 10 mm. Furthermore, the depth of the concave portion 22 is also not particularly limited. However, to generate a sufficient releasing force during the release of the low specific gravity component from the layer structure body and to prevent the specimen from remaining in the concave portion, it is preferable that the mean depth of the concave portion is 0.5 mm or more and it is preferable that the maximum depth of the concave portion is in the range of 0.5 mm to 2 mm. In addition, in terms of the prevention of hemolysis, it is preferable that the inclination of an inner portion of the concave portion 22 is 0.5 mm/mm (that is, $\tan\alpha = 0.5$ and $\alpha$ is about 26.6°) or less from the inclined surface of the inclined inner wall portion 20. Here, the "depth" means a difference between the height of a point, which is positioned in the concave portion 22, and the height of a virtual inclined surface that extends from the inclined inner wall portion 20 so that it is assumed that the concave portion 22 is not formed. Further, the "mean depth" means a value calculated from V/A when the volume of the concave portion 22 (the volume of a space formed by the virtual inclined surface and the concave portion 22) is denoted by V and the projected area of the concave portion 22 on the inclined surface of the inclined inner wall portion 20 (that is, the area of the virtual inclined surface) is denoted by A. Furthermore, the "maximum depth" means the maximum difference between the height of a point, which is positioned in the concave portion 22, and the height of the virtual inclined surface.

Processes of a centrifugal separation method using the centrifugal separation container 1 and the centrifugal separation device 50, which have been described above, will be described below. FIGS. 6A to 6D are schematic sectional views showing the processes of the centrifugal separation method.

Figure 6A:
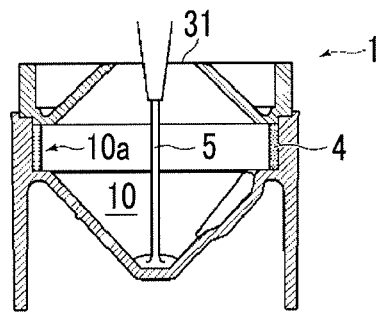
FIGS. 6A to 6D are schematic sectional views showing processes of a centrifugal separation method.
Figure 6B:
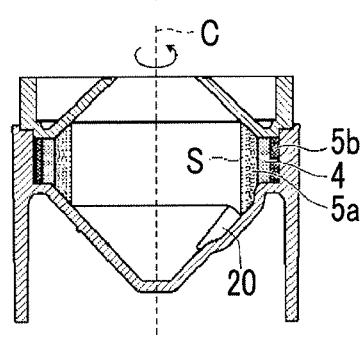
Figure 6C:
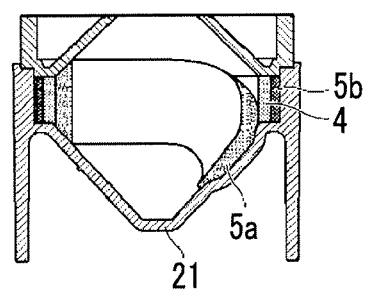
Figure 6D:
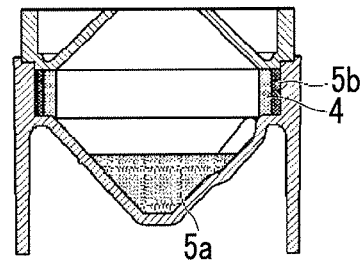

First, the container 1 in which the separating agent 4 is disposed in the trap space 10a in advance is prepared, and a specimen 5 is injected into the storage space 10 from the opening 31 of the container 1 (FIG. 6A). The injection of the specimen 5 is performed using, for example, a pipette or an injector. Next, the container 1 into which the specimen 5 is injected is mounted on the rotating table 53 of the centrifugal separation device 50 and is rotated. At this time, the contents of the container 1 are separated according to specific gravity by a centrifugal force of rotation, and the layer structure body is formed on the outer peripheral side of the storage space 10 (FIG. 6B). The high specific gravity component 5b is trapped in the trap space 10a by trap portions (the trap bottom surface portion 23, the trap side surface portion 26, and the trap upper surface portion 33) and the separating agent 4. Then, when the rotation of the container 1 stops, a portion of the low specific gravity component 5a, which is present above the concave portion 22, starts to be released first due to the presence of the concave portion 22 (FIG. 6C) and other portions are gradually released so as to follow the release of the portion that is present above the concave portion 22. Meanwhile, the high specific gravity component 5b remains in the trap space as it is. Further, when the entire low specific gravity component 5a is released from the layer structure body, the low specific gravity component 5a pools on the lower side in the storage space 10. Accordingly, only the low specific gravity component 5a can be extracted and recovered (FIG. 6D).

As described above, according to the container of this embodiment, a portion of the low specific gravity component, which is present above the concave portion, is more easily released from the layer structure body than portions of the low specific gravity component that are present in other regions. Accordingly, a portion of the low specific gravity component, which is present above the concave portion, is released first from the layer structure body, and portions of the low specific gravity component, which are present in other regions, are released from the layer structure body so as to be pulled to the portion of the low specific gravity component, which is present above the concave portion, due to the release of the portion of the low specific gravity component present above the concave portion. As a result, centrifugally separated components of the specimen can be more efficiently recovered. Further, the concave portion can be easily formed without other members simultaneously with the molding of the container. For this reason, it is possible to reduce manufacturing cost by simplifying processes for manufacturing the container.

Furthermore, since centrifugal separation is performed using the centrifugal separation container of the invention in the centrifugal separation device and the centrifugal separation method of the invention, centrifugally separated components of the specimen can be more efficiently recovered.

OTHER EMBODIMENTS

The body member or the concave portion of the container 1 of the invention is not limited to the structure of the body member or the concave portion of the above-mentioned embodiment.

Figure 7A:
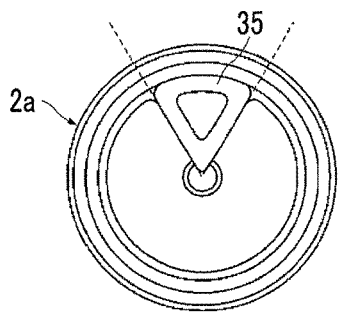
FIGS. 7A to 7E are schematic views showing other structures of a concave portion of the centrifugal separation container.
Figure 7B:
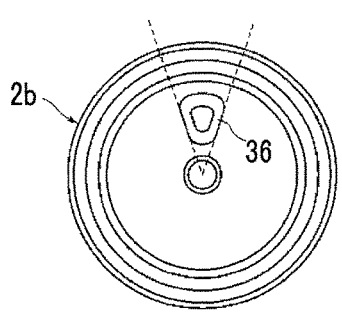

For example, FIG. 7A is a schematic top view showing the structure of a body member 2a including a concave portion 35 of which the shape is different from the shape of the concave portion of the above-mentioned embodiment. The body member 2a of FIG. 7A includes the concave portion 35 that is formed over the base portion 21 from the upper end of the inclined inner wall portion 20. Further, FIG. 7B is a schematic top view showing the structure of a body member 2b including a concave portion 36 of which the shape is different from the shape of the concave portion of the above-mentioned embodiment. The body member 2b of FIG. 7B includes a concave portion 36 that is formed so as to be separated from the upper end of the inclined inner wall portion 20 and the base portion 21.

Figure 7C:
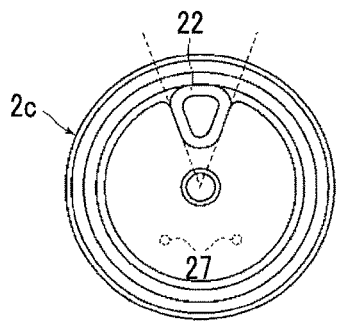

FIG. 7C is a schematic top view showing the structure of a body member 2c of which the shape of a concave portion is the same as that of the embodiment but the disposition of a balancing portion is different from that of the embodiment. The concave portion 22 of FIG. 7C is formed from the upper end of the inclined inner wall portion 20 as in the embodiment. The balancing portion of FIG. 7C is provided with two protrusions 27 each of which is the same as that of the embodiment. Further, the two protrusions 27 are disposed so as to be symmetric to each other with respect to a radial line that passes through the position of the protrusion 27 of the above-mentioned embodiment (that is, the position symmetrical to the position of the concave portion 22 with respect to the central axis C), and balance the container as a whole.

Figure 7D:
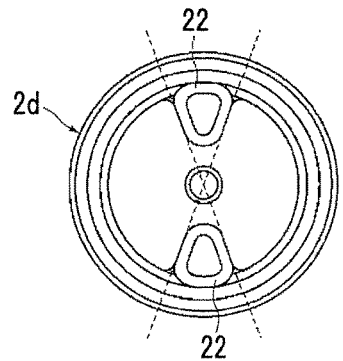
Figure 7E:
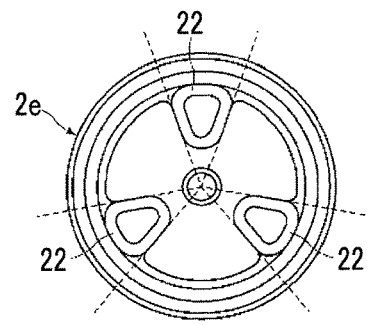

Furthermore, FIGS. 7D and 7E are schematic top views showing the structures of body members 2d and 2e including concave portions each of which has the same shape as the concave portion of the above-mentioned embodiment but of which the number is different from that of the concave portion of the above-mentioned embodiment. Specifically, the body member 2d of FIG. 7D includes two concave portions 22 each of which is the same as the concave portion of the above-mentioned embodiment, and the two concave portions 22 are evenly disposed at an interval of 180°. Meanwhile, the body member 2e of FIG. 7E includes three concave portions 22 each of which is the same as the concave portion of the above-mentioned embodiment, and the three concave portiones 22 are evenly disposed at an interval of 120°. When a plurality of concave portions are evenly disposed as described above, the container can be balanced as a whole. For this reason, a balancing portion is not necessary. For example, the number of the concave portions is appropriately selected according to the capacity of the container (the volume of the storage space) or the range of the specifications of the amount of a specimen.

Figure 8A:
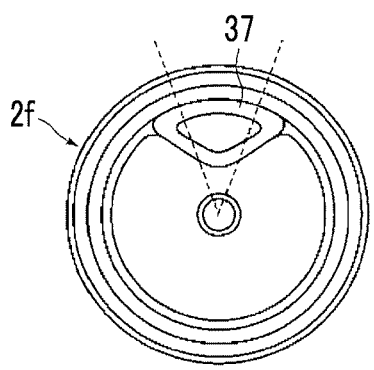
FIGS. 8A and 8B are schematic views showing other structures of the concave portion of the centrifugal separation container.
Figure 8B:
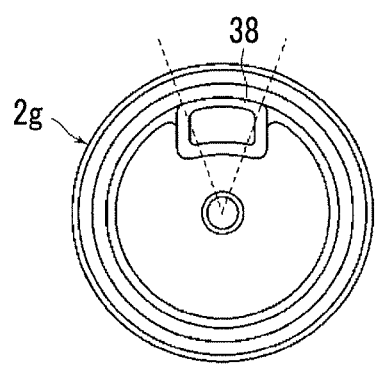

Further, the fan-shaped concave portion having a center on the central axis C has been described in the above-mentioned embodiment and FIGS. 7A to 7E, but the invention is not limited thereto. For example, FIG. 8A is a schematic top view showing the structure of a body member 2f including a fan-shaped concave portion 37 that does not have a center on the central axis C. Furthermore, FIG. 8B is a schematic top view showing the structure of a body member 2g including a substantially rectangular concave portion 38. Effects of the invention are sufficiently obtained even in the cases of the concave portiones having these shapes. However, when the shape of the concave portion is not the shape of a fan as described above, there is a concern that a connecting portion between the concave portion and the other inclined inner wall portion may cause an obstacle when the specimen is centrifuged or when the low specific gravity component moves downward along the inclined surface of the inclined inner wall portion 20. For this reason, it is preferable that the shape of the concave portion is the shape of a fan.

EXAMPLES

Examples of the centrifugal separation method using the centrifugal separation container of the invention will be described below.

Example 1

Figure 9A:
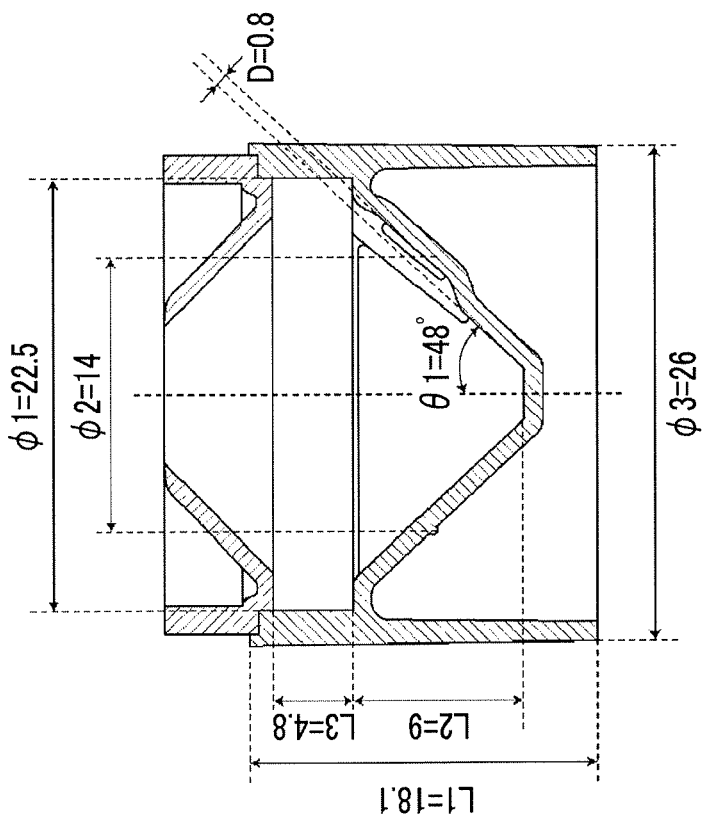
FIGS. 9A and 9B are schematic views showing the structure of a centrifugal separation container according to an example.
Figure 9B:
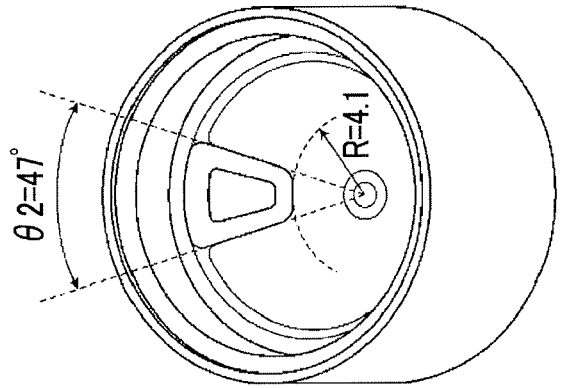

A centrifugal separation container shown in FIGS. 9A and 9B was used in this example. FIG. 9A is a sectional view of the container used in the example, and FIG. 9B is a perspective view of the container. Specific dimensions of the main structure of the container are as follows:

Diameter $\varphi 1$ of a trap space=22.5 mm

Diameter $\varphi 2$ of the circumference including a balancing protrusion=14 mm Diameter $\varphi 3$ of the entire container=26 mm Height L1 of a body member=18.1 mm Depth L2 of a space formed by an inclined inner wall portion=9 mm Height L3 of the trap space=4.8 mm Depth D of a concave portion=0.8 mm Angle $\theta 1$ between an inclined surface of the inclined inner wall portion and a central axis=48°

A circumferential angular range $\theta 2$ occupied by the concave portion=47°

Figure 10A:
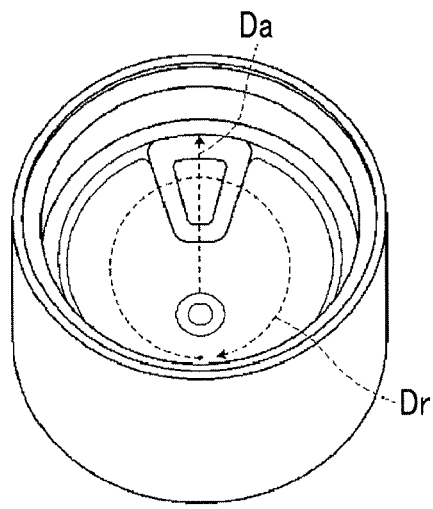
FIGS. 10A to 10C are views showing the sectional profile of a portion near the concave portion based on an inclined surface of an inclined inner wall portion.
Figure 10B:
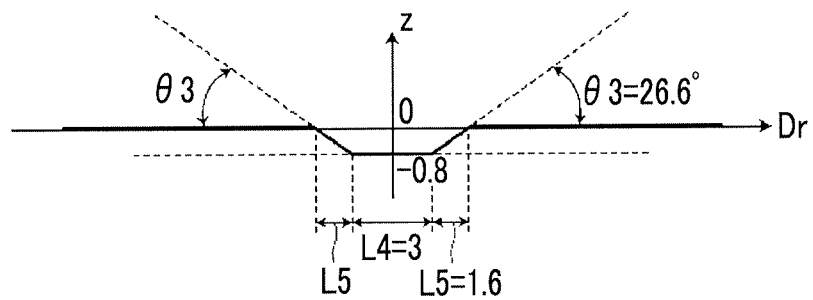
Figure 10C:
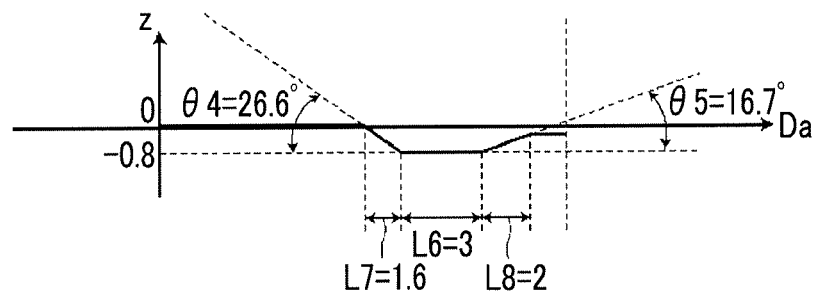

A distance R between a base portion and the concave portion along the inclined surface of the inclined inner wall portion=4.1 mm Further, FIGS. 10A to 10C are views showing the sectional profile of a portion near the concave portion based on an inclined surface of an inclined inner wall portion. FIG. 10A shows two directions (a radial direction Dr and an axial direction Da) along which the section of the concave portion is taken, and FIGS. 10B and 10C show the sectional profile of the concave portion taken along the radial direction Dr and the sectional profile of the concave portion taken along the axial direction Da, respectively. In the centrifugal separation container of the example, the concave portion includes a bottom surface and the width L4 of the base portion is 3 mm at a position where the section is taken. Furthermore, the width L5 of an inclined surface, which connects the bottom surface to a reference surface, (that is, an inclined surface of the inclined inner wall portion) is 1.6 mm and an inclination $\theta 3$ of the inclined surface is about 26.6° ($\tan\theta 3=0.5$). Moreover, the length L6 of the bottom surface of the concave portion in the axial direction Da is 3 mm. Further, the length L7 of an inner peripheral inclined surface, which connects the bottom surface to the reference surface, is 1.6 mm and an inclination $\theta 4$ of the inclined surface is about 26.6°. Meanwhile, the outer peripheral side of the bottom surface is inclined so as to rise by a height of 0.6 mm per 2 mm (L8) (that is, since $\tan\theta 5$ is 0.3, $\theta 5$ is about 16.7°). The concave portion is connected to the trap bottom surface portion while the depth of the concave portion is maintained after the inclination of the concave portion.

600 µL of SCOLLECT (manufactured by Sekisui Medical Co., Ltd.) was dispensed to the centrifugal separation container as a serum separating agent, and 500 µL of whole blood was dispensed. After that, a specimen was centrifuged for 90 seconds (for 110 seconds when 10 seconds at the time of acceleration and 10 seconds at the time of deceleration are included) at a rotational speed of 24000 rpm. Further, the centrifugal separation method was performed twice.

Example 2 and Comparative Example

Centrifugal separation was performed using a container, which included two concave portions, as in Example 2. The concave portions were provided at positions that face each other with a central axis interposed therebetween. Other conditions were the same as those of Example 1. Furthermore, centrifugal separation was performed using a container, which did not include a concave portion and of which an inclined surface of an inclined inner wall portion was flat, as Comparative example. Other conditions were the same as those of Example 1.

<Results>

Figure 11:
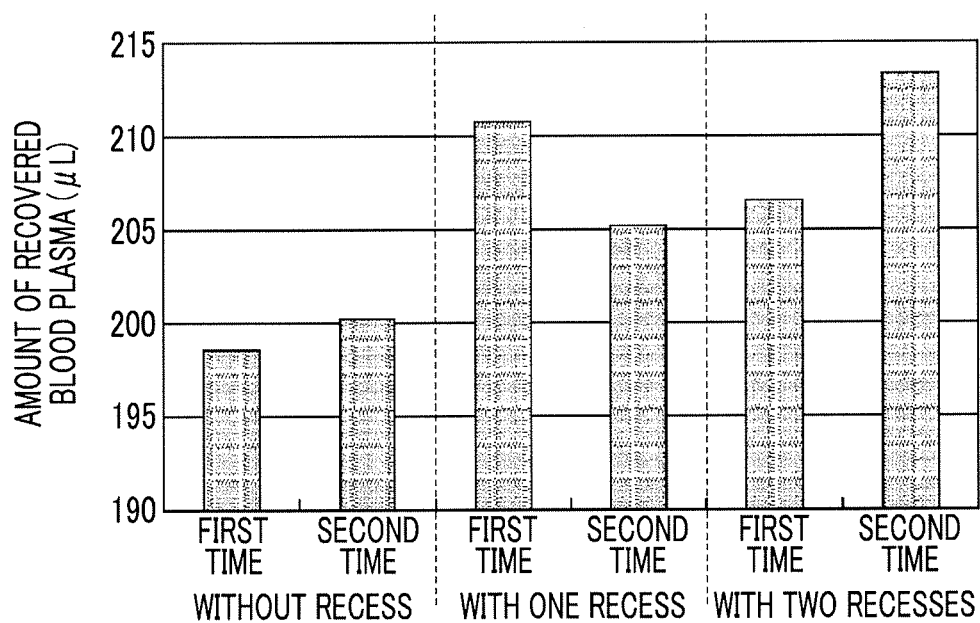
FIG. 11 is a graph showing results of the example.

FIG. 11 is a chart showing the results for the example and the comparative example. It can be understood from this table that more blood plasma can be recovered than for a container not including a concave portion in case where the centrifugal separation container of the invention is used.

EXPLANATION OF REFERENCES

1: centrifugal separation container
2: body member
3: lid member
4: separating agent
5: specimen
5a: low specific gravity component (first specific gravity component)
5b: high specific gravity component (second specific gravity component)
10: storage space
10a: trap space
20: inner wall portion
21: base portion
22: concave portion
22a: concave portion bottom surface
22b: concave portion side surface
23: trap bottom surface portion
24: fitting portion
25: outer support wall portion
26: trap side surface portion
27: protrusion
30: opening portion
31: opening
33: surface portion
50: centrifugal separation device
R: rotation axis
S: interface
W1: maximum width
W2: maximum length

What is claimed is:

1. A centrifugal separation method, using a centrifugal separation container, which centrifugally separating a first specific gravity component and a second specific gravity component, of which a specific gravity of the second gravity component is higher than a specific gravity of the first specific gravity component, contained in a specimen injected into a storage space by rotating a container about a central axis of the container as a rotation axis, the centrifugal separation method comprising:
   injecting a specimen into a storage portion that forms the storage space in the centrifugal separation container,
   wherein the storage portion includes an inclined inner wall portion of which a diameter gradually decreases from an upper end toward a lower end thereof and the lower end is connected to a base portion, and
   a concave portion formed at a part of the inclined inner wall portion,
   the concave portion includes a concave portion side surface that is connected to a concave portion bottom surface with a width of the concave portion gradually decreases toward the concave portion bottom surface from the inclined inner wall portion;
   rotating the centrifugal separation container about the central axis of the container as a rotation axis,
   wherein an interface between the specimen centrifuged during rotation and air, in a radial direction with respect to the central axis crosses where the concave portion is formed.

2. The centrifugal separation method according to claim 1,
   wherein a connecting portion between the inclined inner wall portion and the concave portion side surface has a curvature.

3. The centrifugal separation method according to claim 1,
   wherein a connecting portion between the concave portion side surface and the concave portion bottom surface has a curvature.

4. The centrifugal separation method according to claim 2,
   wherein a connecting portion between the concave portion side surface and the concave portion bottom surface has a curvature.

5. The centrifugal separation method according to claim 1,
   wherein a mean depth of the concave portion is 0.5 mm or more.

6. The centrifugal separation method according to claim 2,
   wherein a mean depth of the concave portion is 0.5 mm or more.

7. The centrifugal separation method according to claim 1,
   wherein the maximum depth of the concave portion is in the range of 0.5 mm to 2 mm.

8. The centrifugal separation method according to claim 1,
   wherein the maximum width of the concave portion is 10 mm or less.

9. The centrifugal separation method according to claim 1,
   wherein the concave portion has the shape of a fan.

10. The centrifugal separation method according to claim 1,
    wherein one concave portion is formed.

11. The centrifugal separation method according to claim 10, further comprising:
    a balancing portion that offsets a deviation of the center of gravity from the central axis caused by the formation of the concave portion to balance the container.

12. The centrifugal separation method according to claim 11,
    wherein the balancing portion is provided on the inclined inner wall portion at a position that is symmetrical to the position of the concave portion with respect to the central axis.

13. The centrifugal separation method according to claim 1,
    wherein two to four concave portions are formed.

14. The centrifugal separation method according to claim 13,
    wherein the concave portions are evenly disposed in the circumferential direction.

15. The centrifugal separation method according to claim 1,
    wherein the maximum length of the concave portion is in the range of 5 mm to 15 mm.

16. The centrifugal separation method according to claim 1,
    wherein the concave portion is formed from the uppermost portion of the inclined inner wall portion.

17. The centrifugal separation method according to claim 1,
    wherein the storage portion includes a trap portion that is connected to an upper end of the inclined inner wall portion and forms a trap space housing the second specific gravity component when the specimen is centrifugally separated and a layer structure body is formed on an outer peripheral side of the storage space.

18. The centrifugal separation method according to claim 1,
wherein a thixotropic separating agent, which has a specific gravity between the specific gravity of the first specific gravity component and the specific gravity of the second specific gravity component, is provided in the storage space.

19. A centrifugal separation method comprising:
the centrifugal separation method according to claim 1; and
a step of holding the container by a container holder that rotates about a central axis of the container as a rotation axis.

\* \* \* \* \*